United States Patent
Hamlin

[19]

[11] Patent Number: 6,132,824
[45] Date of Patent: *Oct. 17, 2000

[54] MULTILAYER CATHETER BALLOON

[75] Inventor: Robert N. Hamlin, Stillwater, Minn.

[73] Assignee: Schneider (USA) Inc.

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/907,170

[22] Filed: Aug. 6, 1997

Related U.S. Application Data

[62] Division of application No. 08/692,314, Aug. 5, 1996, which is a continuation of application No. 08/415,094, Mar. 31, 1995, abandoned, which is a continuation of application No. 08/105,353, Aug. 10, 1993, abandoned, which is a division of application No. 07/727,664, Jul. 9, 1991, Pat. No. 5,270,086, which is a continuation-in-part of application No. 07/411,649, Sep. 25, 1989, abandoned.

[51] Int. Cl.$^7$ .................................................. A61M 29/02
[52] U.S. Cl. .................... 428/35.2; 428/36.9; 428/36.91; 606/192; 604/96
[58] Field of Search ................................. 428/35.2, 36.9, 428/36.91; 606/192; 604/96

[56] References Cited

U.S. PATENT DOCUMENTS

| | | | |
|---|---|---|---|
| Re. 33,561 | 3/1991 | Levy | 428/36.92 |
| 1,643,289 | 9/1927 | Peglay | 604/192 |
| 1,690,995 | 11/1928 | Pratt | 606/192 |
| 2,499,045 | 2/1950 | Walker et al. | 128/261 |
| 2,548,602 | 4/1951 | Greenburg | 128/4 |
| 2,616,429 | 11/1952 | Merenlender | 128/350 |
| 2,688,329 | 9/1954 | Wallace | 128/349 |
| 2,690,595 | 10/1954 | Raiche | 18/59.7 |
| 2,799,273 | 7/1957 | Oddo | 128/325 |

(List continued on next page.)

FOREIGN PATENT DOCUMENTS

| | | |
|---|---|---|
| 1566776 | 11/1976 | Australia . |
| 0 101 216 A2 | 2/1984 | European Pat. Off. . |
| 0 166 998 | 1/1986 | European Pat. Off. . |
| 0 174 206 A2 | 3/1986 | European Pat. Off. . |
| 0 201 331 A2 | 11/1986 | European Pat. Off. . |
| 0214721A1 | 3/1987 | European Pat. Off. . |
| 0 266 957 A2 | 5/1988 | European Pat. Off. . |
| 0274411A2 | 7/1988 | European Pat. Off. . |
| 0 276 908 A1 | 8/1988 | European Pat. Off. . |
| 0 303 487 A2 | 2/1989 | European Pat. Off. . |
| 0 329 041 A2 | 8/1989 | European Pat. Off. . |

(List continued on next page.)

OTHER PUBLICATIONS

Parker, "Coextruded Composite Film", Modern Plastics Encyclopedia, Oct. 1973, pp. 155 & 156.

"Polymer Structure, Properties and Applications", Rudolph D. Deanin, Ph.D., Professor of Plastics, Lowell Technological Institute, Table of Contents and pp. 196–220.

"Mechanics of Materials", Third Edition, James M. Gere, Stanford University, pp. 52–59.

Adrova et al., "Polymides: A new Class of Heat–Resistant Polymers", Academy of Sciences of the USSR, Chapter 1, "Synthesis and Transformations of Polymides", pp. 1–36, 1969.

(List continued on next page.)

*Primary Examiner*—Rena L. Dye
*Attorney, Agent, or Firm*—Fish & Richardson P.C.

[57] ABSTRACT

A method of producing laminated inflatable, substantially inextensible expander members having composite properties enhancing their use on intravascular catheters, such as angioplasty catheters is described. Diverse polymeric compounds of differing properties are coextruded to create a multilayer parison. The parison is subsequently drawn and expanded in a blow molding operation to yield an expander member exhibiting enhanced properties including lubricity, burst-strength, limited radial expansion, bondability, and rupture characteristics.

25 Claims, 6 Drawing Sheets

U.S. PATENT DOCUMENTS

| | | | |
|---|---|---|---|
| 2,823,421 | 2/1958 | Scarlett | 18/57 |
| 2,936,760 | 5/1960 | Gants | 128/349 |
| 2,981,254 | 4/1961 | Vanderbilt | 128/350 |
| 3,045,677 | 7/1962 | Wallace | 128/349 |
| 3,053,257 | 9/1962 | Birtwell | 128/349 |
| 3,141,912 | 7/1964 | Goldman et al. | 264/95 |
| 3,173,418 | 3/1965 | Baran | 128/351 |
| 3,292,627 | 12/1966 | Harautuneian | 128/349 |
| 3,304,353 | 2/1967 | Harautuneian | 264/98 |
| 3,348,542 | 10/1967 | Jackson | 128/184 |
| 3,426,744 | 2/1969 | Ball | 128/1 |
| 3,432,591 | 3/1969 | Heffelfinger | 128/289 |
| 3,539,674 | 11/1970 | Derenuik et al. | 264/130 |
| 3,543,758 | 12/1970 | McWhorter | 128/349 |
| 3,543,759 | 12/1970 | McWhorter | 128/349 |
| 3,561,493 | 2/1971 | Maillard | 138/141 |
| 3,562,352 | 2/1971 | Nyilas | 260/824 |
| 3,618,614 | 11/1971 | Flynn | 128/348 |
| 3,707,146 | 12/1972 | Cook et al. | 600/593 |
| 3,707,151 | 12/1972 | Jackson | 128/351 |
| 3,707,590 | 12/1972 | Wiggins et al. | 264/95 |
| 3,731,692 | 5/1973 | Goodyear | 128/351 |
| 3,733,309 | 5/1973 | Wyeth et al. | 260/75 |
| 3,745,150 | 7/1973 | Corsover | 260/75 |
| 3,769,984 | 11/1973 | Muench | 128/404 |
| 3,771,527 | 11/1973 | Ruisi | 604/43 |
| 3,799,172 | 3/1974 | Szpur | 128/349 R |
| 3,807,408 | 4/1974 | Summers | 604/104 |
| 3,814,137 | 6/1974 | Martinez | 138/103 |
| 3,833,004 | 9/1974 | Vazquez et al. | 128/349 B |
| 3,837,347 | 9/1974 | Tower | 128/404 |
| 3,861,972 | 1/1975 | Glover et al. | 156/86 |
| 3,889,685 | 6/1975 | Miller, Jr. et al. | 128/348 |
| 3,924,634 | 12/1975 | Taylor et al. | 128/349 B |
| 3,959,426 | 5/1976 | Seefluth | 264/94 |
| 3,962,519 | 6/1976 | Rusch et al. | 428/409 |
| 3,996,938 | 12/1976 | Clark, III | 128/34 |
| 4,003,382 | 1/1977 | Dyke | 128/349 B |
| 4,011,189 | 3/1977 | Keil | 260/33.6 |
| 4,035,534 | 7/1977 | Nyberg | 428/36 |
| 4,047,868 | 9/1977 | Kudo et al. | 425/133.1 |
| 4,055,682 | 10/1977 | Merrill | 427/2 |
| 4,061,707 | 12/1977 | Nohtomi et al. | 264/95 |
| 4,079,850 | 3/1978 | Suzuki et al. | 215/1 C |
| 4,085,757 | 4/1978 | Pevsner | 128/325 |
| 4,105,022 | 8/1978 | Antoshkiw et al. | 128/2.05 |
| 4,140,126 | 2/1979 | Choudhury | 128/325 |
| 4,141,364 | 2/1979 | Schultz | 128/349 B |
| 4,144,298 | 3/1979 | Lee | 264/532 |
| 4,174,783 | 11/1979 | Abe et al. | 215/1 C |
| 4,182,457 | 1/1980 | Yamada | 215/1 |
| 4,183,102 | 1/1980 | Guiset | 3/1.4 |
| 4,195,637 | 4/1980 | Gruntzig et al. | 128/348 |
| 4,198,981 | 4/1980 | Sinnreich | 128/344 |
| 4,211,741 | 7/1980 | Ostoich | 264/173 |
| 4,213,461 | 7/1980 | Pevsner | 128/348 |
| 4,222,384 | 9/1980 | Birtwell | 128/349 B |
| 4,233,022 | 11/1980 | Brady et al. | 425/525 |
| 4,238,443 | 12/1980 | Levy | 264/210.7 |
| 4,244,914 | 1/1981 | Ranalli et al. | 264/515 |
| 4,251,305 | 2/1981 | Becker et al. | 264/515 |
| 4,256,789 | 3/1981 | Suzuki et al. | 428/35 |
| 4,261,339 | 4/1981 | Hanson et al. | 128/1 D |
| 4,263,188 | 4/1981 | Hampton et al. | 260/29.2 |
| 4,265,276 | 5/1981 | Hatada et al. | 138/177 |
| 4,265,848 | 5/1981 | Rüsch | 264/130 |
| 4,271,839 | 6/1981 | Fogarty et al. | 128/344 |
| 4,282,876 | 8/1981 | Flynn | 128/349 |
| 4,292,974 | 10/1981 | Fogarty et al. | 128/344 |
| 4,296,156 | 10/1981 | Lustig et al. | 428/35 |
| 4,299,226 | 11/1981 | Banka | 128/344 |
| 4,300,550 | 11/1981 | Gandi et al. | 128/207.18 |
| 4,301,053 | 11/1981 | Wolfrey | 260/29.2 |
| 4,306,998 | 12/1981 | Wenzel et al. | 260/13 |
| 4,318,947 | 3/1982 | Joung | 528/399 |
| 4,323,071 | 4/1982 | Simpson et al. | 128/343 |
| 4,324,262 | 4/1982 | Hall | 128/756 |
| 4,326,532 | 4/1982 | Hammer | 128/349 R |
| 4,327,736 | 5/1982 | Inoue | 128/349 B |
| 4,330,497 | 5/1982 | Agdanowski | 264/150 |
| 4,335,723 | 6/1982 | Patel | 604/97 |
| 4,338,942 | 7/1982 | Fogarty | 606/194 |
| 4,346,698 | 8/1982 | Hanson et al. | 128/1 D |
| 4,351,341 | 9/1982 | Goldberg et al. | 128/348 |
| 4,378,803 | 4/1983 | Takagi et al. | 604/280 |
| 4,385,089 | 5/1983 | Bonnebat et al. | 428/35 |
| 4,403,612 | 9/1983 | Fogarty | 128/344 |
| 4,406,653 | 9/1983 | Nunez | 604/103 |
| 4,406,656 | 9/1983 | Hattler et al. | 604/280 |
| 4,409,364 | 10/1983 | Schmukler et al. | 525/74 |
| 4,411,055 | 10/1983 | Simpson et al. | 29/447 |
| 4,413,989 | 11/1983 | Schjeldahl et al. | 604/96 |
| 4,417,576 | 11/1983 | Baran | 128/207.15 |
| 4,422,447 | 12/1983 | Schiff | 128/1 D |
| 4,423,725 | 1/1984 | Baran et al. | 128/207.15 |
| 4,424,242 | 1/1984 | Barbee | 428/35 |
| 4,434,797 | 3/1984 | Silander | 128/343 |
| 4,439,394 | 3/1984 | Appleyard | 264/535 |
| 4,444,188 | 4/1984 | Bazell et al. | 128/348.1 |
| 4,451,256 | 5/1984 | Weikl et al. | 128/325 |
| 4,456,011 | 6/1984 | Warnecke | 128/325 |
| 4,472,129 | 9/1984 | Siard | 425/381 |
| 4,479,497 | 10/1984 | Fogarty et al. | 128/344 |
| 4,484,971 | 11/1984 | Wang | 156/244.14 |
| 4,490,421 | 12/1984 | Levy | 428/36.9 |
| 4,497,074 | 2/1985 | Rey et al. | 3/1 |
| 4,521,564 | 6/1985 | Solomon et al. | 525/54.1 |
| 4,531,997 | 7/1985 | Johnston | 156/498 |
| 4,540,404 | 9/1985 | Wolvek | 604/96 |
| 4,551,292 | 11/1985 | Fletcher et al | 264/139 |
| 4,553,545 | 11/1985 | Maass | 128/341 |
| 4,559,951 | 12/1985 | Dahl et al. | 128/642 |
| 4,572,186 | 2/1986 | Gould et al. | 128/341 |
| 4,573,470 | 3/1986 | Samson et al. | 128/344 |
| 4,573,966 | 3/1986 | Weikl et al. | 604/53 |
| 4,576,142 | 3/1986 | Schiff | 128/1 D |
| 4,576,772 | 3/1986 | Carpenter | 264/154 |
| 4,578,024 | 3/1986 | Sicka et al. | 425/114 |
| 4,579,879 | 4/1986 | Flynn | 523/112 |
| 4,581,390 | 4/1986 | Flynn | 523/112 |
| 4,582,762 | 4/1986 | Onohara et al. | 428/477 |
| 4,585,000 | 4/1986 | Hershenson | 128/345 |
| 4,596,563 | 6/1986 | Pande | 604/264 |
| 4,606,347 | 8/1986 | Fogarty et al. | 128/344 |
| 4,608,984 | 9/1986 | Fogarty | 128/344 |
| 4,610,662 | 9/1986 | Weikl et al. | 604/53 |
| 4,613,517 | 9/1986 | Williams et al. | 427/2 |
| 4,614,188 | 9/1986 | Bazell et al. | 128/348.1 |
| 4,627,436 | 12/1986 | Leckrone | 128/303.1 |
| 4,627,844 | 12/1986 | Schmitt | 604/264 |
| 4,634,615 | 1/1987 | Versteegh et al. | 428/36 |
| 4,636,346 | 1/1987 | Gold et al. | 264/139 |
| 4,636,442 | 1/1987 | Beavers et al. | 428/480 |
| 4,637,396 | 1/1987 | Cook | 128/344 |
| 4,638,805 | 1/1987 | Powell | 128/344 |
| 4,640,852 | 2/1987 | Ossian | 428/35 |
| 4,642,267 | 2/1987 | Creasy et al. | 428/413 |
| 4,648,871 | 3/1987 | Jacob | 604/149 |
| 4,650,466 | 3/1987 | Luther | 604/95 |
| 4,651,721 | 3/1987 | Mikulich et al. | 128/79 |
| 4,655,745 | 4/1987 | Corbett | 604/49 |
| 4,655,771 | 4/1987 | Wallsten | 623/1 |

| | | | | | | | |
|---|---|---|---|---|---|---|---|
| 4,656,070 | 4/1987 | Nyberg et. al | 428/36 | 4,900,303 | 2/1990 | Lemelson | 604/54 |
| 4,657,024 | 4/1987 | Coneys | 128/658 | 4,906,237 | 3/1990 | Johansson et al. | 604/265 |
| 4,660,560 | 4/1987 | Klein | 128/344 | 4,906,241 | 3/1990 | Noddin et al. | 606/194 |
| 4,664,657 | 5/1987 | Williamitis et al. | 604/265 | 4,906,244 | 3/1990 | Pinchuk et al. | 604/96 |
| 4,666,437 | 5/1987 | Lambert | 604/265 | 4,909,252 | 3/1990 | Goldberger | 606/194 |
| 4,677,017 | 6/1987 | DeAntonis et al. | 428/214 | 4,913,701 | 4/1990 | Tower | 604/103 |
| 4,681,564 | 7/1987 | Landreneau | 604/97 | 4,921,479 | 5/1990 | Grayzel | 604/509 |
| 4,684,363 | 8/1987 | Ari et al. | 606/192 | 4,921,483 | 5/1990 | Wijay et al. | 604/96 |
| 4,685,447 | 8/1987 | Iversen et al. | 128/1 | 4,923,450 | 5/1990 | Maeda et al. | 604/265 |
| 4,685,458 | 8/1987 | Leckrone | 128/303.1 | 4,932,956 | 6/1990 | Reddy et al. | 606/192 |
| 4,686,124 | 8/1987 | Onohara et al. | 428/35 | 4,932,958 | 6/1990 | Reddy et al. | 606/192 |
| 4,693,243 | 9/1987 | Buras | 128/207.15 | 4,933,178 | 6/1990 | Capelli | 424/78 |
| 4,699,611 | 10/1987 | Bowden | 606/191 | 4,934,999 | 6/1990 | Bader | 600/29 |
| 4,702,252 | 10/1987 | Brooks et al. | 606/195 | 4,938,676 | 7/1990 | Jackowski et al. | 425/140 |
| 4,705,502 | 11/1987 | Patel | 604/49 | 4,941,877 | 7/1990 | Montano, Jr. | 604/96 |
| 4,705,517 | 11/1987 | DiPesa, Jr. | 623/12 | 4,946,464 | 8/1990 | Pevsner | 606/192 |
| 4,705,709 | 11/1987 | Vailancourt | 428/36.91 | 4,946,466 | 8/1990 | Pinchuk et al. | 604/96 |
| 4,706,670 | 11/1987 | Andersen et al. | 128/344 | 4,950,227 | 8/1990 | Savin et al. | 604/8 |
| 4,710,181 | 12/1987 | Fuqua | 604/265 | 4,950,239 | 8/1990 | Gahara et al. | 604/96 |
| 4,723,936 | 2/1988 | Buchbinder et al. | 604/95 | 4,952,357 | 8/1990 | Euteneuer | 604/96 |
| 4,729,914 | 3/1988 | Kliment et al. | 428/35.7 | 4,954,126 | 9/1990 | Wallsten | 600/36 |
| 4,732,153 | 3/1988 | Wallsten | 128/343 | 4,960,410 | 10/1990 | Pinchuk | 604/96 |
| 4,737,219 | 4/1988 | Taller et al. | 156/215 | 4,963,306 | 10/1990 | Weldon | 264/101 |
| 4,743,257 | 5/1988 | Tormala et al. | 623/16 | 4,963,313 | 10/1990 | Noddin et al. | 264/573 |
| 4,744,366 | 5/1988 | Jang | 606/192 | 4,964,853 | 10/1990 | Sugiyama et al. | 604/96 |
| 4,751,924 | 6/1988 | Hammerschmidt et al. | 128/207.15 | 4,973,301 | 11/1990 | Nissenkorn | 604/8 |
| 4,753,765 | 6/1988 | Pande | 264/149 | 4,986,830 | 1/1991 | Owens et al. | 606/194 |
| 4,762,129 | 8/1988 | Bonzel | 128/344 | 4,994,033 | 2/1991 | Shockey et al. | 604/101 |
| 4,762,130 | 8/1988 | Fogarty et al. | 128/348.1 | 4,994,047 | 2/1991 | Walker et al. | 606/264 |
| 4,762,589 | 8/1988 | Akiyama et al. | 156/307.3 | 4,994,072 | 2/1991 | Bhate et al. | 606/194 |
| 4,763,653 | 8/1988 | Rockey | 128/344 | 4,995,868 | 2/1991 | Brazier | 604/105 |
| 4,771,776 | 9/1988 | Powell et al. | 128/344 | 5,000,734 | 3/1991 | Boussignac et al. | 604/96 |
| 4,771,778 | 9/1988 | Mar | 128/344 | 5,002,531 | 3/1991 | Bonzel | 604/96 |
| 4,773,901 | 9/1988 | Norton | 604/265 | 5,002,556 | 3/1991 | Ishida et al. | 606/191 |
| 4,775,371 | 10/1988 | Mueller, Jr. | 604/280 | 5,006,119 | 4/1991 | Acker et al. | 606/27 |
| 4,776,337 | 10/1988 | Palmaz | 128/344 | 5,015,231 | 5/1991 | Kieth et al. | 604/96 |
| 4,778,697 | 10/1988 | Geneske et al. | 428/35.2 | 5,017,325 | 5/1991 | Jackowski et al. | 264/521 |
| 4,786,556 | 11/1988 | Hu et al. | 428/412 | 5,026,607 | 6/1991 | Kiezulas | 428/423.7 |
| 4,787,388 | 11/1988 | Hofmann | 128/344 | 5,035,694 | 7/1991 | Kasprzyk | 606/192 |
| 4,790,831 | 12/1988 | Skriniski | 604/524 | 5,037,392 | 8/1991 | Hillstead | 604/96 |
| 4,795,458 | 1/1989 | Regan | 623/1 | 5,041,089 | 8/1991 | Muelier et al. | 604/96 |
| 4,796,629 | 1/1989 | Grayzel | 128/344 | 5,041,100 | 8/1991 | Rowland | 604/265 |
| 4,800,882 | 1/1989 | Gianturco | 128/343 | 5,041,125 | 8/1991 | Montano, Jr. | 606/192 |
| 4,801,297 | 1/1989 | Mueller | 604/280 | 5,042,985 | 8/1991 | Elliott et al. | 606/192 |
| 4,803,035 | 2/1989 | Kresge et al. | 264/519 | 5,049,132 | 9/1991 | Shaffer et al. | 604/101 |
| 4,807,626 | 2/1989 | McGirr | 606/127 | 5,057,092 | 10/1991 | Webster, Jr. | 604/282 |
| 4,810,543 | 3/1989 | Gould et al. | 428/35.7 | 5,057,106 | 10/1991 | Kasevich et al. | 606/33 |
| 4,811,737 | 3/1989 | Rydell | 128/344 | 5,059,269 | 10/1991 | Hu et al. | 156/244.11 |
| 4,814,231 | 3/1989 | Onohara et al. | 428/425.5 | 5,061,424 | 10/1991 | Karimi et al. | 264/171 |
| 4,816,339 | 3/1989 | Tu et al. | 428/421 | 5,071,406 | 12/1991 | Jang | 604/96 |
| 4,818,592 | 4/1989 | Ossian | 428/216 | 5,071,686 | 12/1991 | Genske et al. | 428/35.7 |
| 4,819,751 | 4/1989 | Shimada et al. | 128/344 | 5,074,840 | 12/1991 | Yoon | 604/15 |
| 4,820,349 | 4/1989 | Saab | 128/344 | 5,074,845 | 12/1991 | Miraki et al. | 604/15 |
| 4,821,722 | 4/1989 | Miller et al. | 128/344 | 5,075,152 | 12/1991 | Tsukuda et al. | 428/204 |
| 4,824,618 | 4/1989 | Strum et al. | 264/37 | 5,077,352 | 12/1991 | Elton | 525/409 |
| 4,834,702 | 5/1989 | Rocco | 604/43 | 5,078,702 | 1/1992 | Pomeranz | 604/524 |
| 4,834,721 | 5/1989 | Onohara et al. | 604/266 | 5,084,315 | 1/1992 | Karimi et al. | 428/36.6 |
| 4,835,089 | 5/1989 | Bonnebat | 430/323 | 5,087,244 | 2/1992 | Wolinsky et al. | 604/53 |
| 4,838,876 | 6/1989 | Wong et al. | 604/265 | 5,087,246 | 2/1992 | Smith | 604/96 |
| 4,840,623 | 6/1989 | Quackenbush | 604/280 | 5,090,958 | 2/1992 | Sahota | 604/98 |
| 4,846,812 | 7/1989 | Walker et al. | 604/264 | 5,091,205 | 2/1992 | Fan | 427/2 |
| 4,856,516 | 8/1989 | Hillstead | 128/343 | 5,093,164 | 3/1992 | Bauer et al. | 428/35.4 |
| 4,857,393 | 8/1989 | Kato et al. | 428/289 | 5,094,799 | 3/1992 | Takashige et al. | 264/514 |
| 4,863,426 | 9/1989 | Ferragamo et al. | 604/93 | 5,100,381 | 3/1992 | Burns | 604/96 |
| 4,868,044 | 9/1989 | Tanaka et al. | 428/304.4 | 5,100,386 | 3/1992 | Inoue | 604/103 |
| 4,869,263 | 9/1989 | Segal et al. | 128/692 | 5,100,721 | 3/1992 | Akao | 428/218 |
| 4,871,094 | 10/1989 | Gall et al. | 222/386 | 5,100,992 | 3/1992 | Cohn et al. | 528/26 |
| 4,878,495 | 11/1989 | Grayzel | 128/344 | 5,102,416 | 4/1992 | Rock | 606/194 |
| 4,880,682 | 11/1989 | Hazelton et al. | 428/152 | 5,108,415 | 4/1992 | Pinchuk et al. | 606/194 |
| 4,886,062 | 12/1989 | Wiktor | 128/343 | 5,108,420 | 4/1992 | Marks | 606/213 |
| 4,896,669 | 1/1990 | Bhate et al. | 606/194 | 5,114,423 | 5/1992 | Kasprzyk et al. | 606/27 |
| 4,898,591 | 2/1990 | Jang et al. | 604/282 | 5,116,318 | 5/1992 | Hillstead | 604/96 |

| | | | |
|---|---|---|---|
| 5,125,913 | 6/1992 | Quakenbush | 604/264 |
| 5,137,512 | 8/1992 | Burns et al. | 606/96 |
| 5,147,302 | 9/1992 | Euteneuer et al. | 604/103 |
| 5,156,857 | 10/1992 | Wang et al. | 425/130 |
| 5,160,321 | 11/1992 | Sahota | 604/96 |
| 5,163,949 | 11/1992 | Bonutti | 606/192 |
| 5,171,221 | 12/1992 | Samson | 604/96 |
| 5,176,697 | 1/1993 | Hasson et al. | 606/191 |
| 5,179,174 | 1/1993 | Elton | 525/409 |
| 5,183,613 | 2/1993 | Edwards | 264/171 |
| 5,192,296 | 3/1993 | Bhate et al. | 604/194 |
| 5,195,969 | 3/1993 | Wang et al. | 604/96 |
| 5,195,970 | 3/1993 | Gahara | 604/96 |
| 5,195,972 | 3/1993 | Inoue | 604/103 |
| 5,201,706 | 4/1993 | Noguchi et al. | 604/96 |
| 5,209,728 | 5/1993 | Kraus et al. | 604/96 |
| 5,223,205 | 6/1993 | Jackowski et al. | 264/521 |
| 5,226,880 | 7/1993 | Martin | 604/99 |
| 5,248,305 | 9/1993 | Zdrahala | 604/280 |
| 5,254,090 | 10/1993 | Lombardi et al. | 604/96 |
| 5,254,091 | 10/1993 | Aliahmad et al. | 604/96 |
| 5,263,962 | 11/1993 | Johnson et al. | 606/192 |
| 5,270,086 | 12/1993 | Hamlin | 428/35.2 |
| 5,272,012 | 12/1993 | Opolski | 428/423.1 |
| 5,277,199 | 1/1994 | DuBois et al. | 128/772 |
| 5,279,560 | 1/1994 | Morrill et al. | 604/96 |
| 5,279,594 | 1/1994 | Jackson | 604/265 |
| 5,290,306 | 3/1994 | Trotta et al. | 606/194 |
| 5,304,171 | 4/1994 | Gregory et al. | 606/15 |
| 5,304,197 | 4/1994 | Pinchuk | 606/194 |
| 5,306,246 | 4/1994 | Sahatjian et al. | 604/96 |
| 5,312,356 | 5/1994 | Engelson et al. | 604/164 |
| 5,318,041 | 6/1994 | DuBois et al. | 607/119 |
| 5,318,587 | 6/1994 | Davey | 606/194 |
| 5,330,428 | 7/1994 | Wang et al. | 604/96 |
| 5,330,429 | 7/1994 | Noguchi | 604/96 |
| 5,334,146 | 8/1994 | Ozasa | 604/96 |
| 5,342,307 | 8/1994 | Euteneuer et al. | 604/103 |
| 5,344,401 | 9/1994 | Radisch et al. | 604/96 |
| 5,358,486 | 10/1994 | Saab | 604/96 |
| 5,364,357 | 11/1994 | Aase | 604/96 |
| 5,366,472 | 11/1994 | Hillstead | 606/194 |
| 5,372,603 | 12/1994 | Acker et al. | 606/194 |
| 5,413,559 | 5/1995 | Sirham et al. | 604/102 |
| 5,417,671 | 5/1995 | Jackson | 604/265 |
| 5,509,899 | 4/1996 | Fan et al. | 604/96 |

FOREIGN PATENT DOCUMENTS

| | | |
|---|---|---|
| 0 357 562 | 3/1990 | European Pat. Off. . |
| 0 358 445 A2 | 3/1990 | European Pat. Off. . |
| 0 359 489 A2 | 3/1990 | European Pat. Off. . |
| 0 414 350 B1 | 3/1990 | European Pat. Off. . |
| 0 380 102 A1 | 8/1990 | European Pat. Off. . |
| 0 383 429 | 8/1990 | European Pat. Off. . |
| 0 399 712 A1 | 11/1990 | European Pat. Off. . |
| 0 419 291 A1 | 3/1991 | European Pat. Off. . |
| 0 439 202 A2 | 7/1991 | European Pat. Off. . |
| 0 457 456 A1 | 11/1991 | European Pat. Off. . |
| 2635785A1 | 4/1977 | Germany . |
| 31 24 198 A1 | 4/1992 | Germany . |
| 50 75256 | 6/1975 | Japan . |
| 51 084877 | 7/1976 | Japan . |
| 5128668 | 8/1976 | Japan . |
| 539887 | 1/1978 | Japan . |
| 53 042256 | 4/1978 | Japan . |
| 5345353 | 4/1978 | Japan . |
| 5345353 | 12/1978 | Japan . |
| 58 38778 | 3/1983 | Japan . |
| 58118766 | 7/1983 | Japan . |
| 58188463 | 11/1983 | Japan . |
| 63 087219 | 4/1988 | Japan . |
| 6326655 | 5/1988 | Japan . |
| 63183070 | 7/1988 | Japan . |
| 3 277374 | 12/1991 | Japan . |
| 4505569 | 10/1992 | Japan . |
| 2255027 | 10/1993 | Japan . |
| 069826 | 1/1984 | U.S.S.R. . |
| 693244 | 6/1953 | United Kingdom . |
| 1533204 | 11/1978 | United Kingdom . |
| 1 556 242 | 11/1979 | United Kingdom . |
| 1556242 | 11/1979 | United Kingdom . |
| 1600963 | 10/1981 | United Kingdom . |
| 2 077 111 | 12/1981 | United Kingdom . |
| 2 078 114 | 1/1982 | United Kingdom . |
| 2130093 | 5/1984 | United Kingdom . |
| 2 140 437 | 11/1984 | United Kingdom . |
| 2 163 386 | 2/1986 | United Kingdom . |
| 2209121 | 5/1989 | United Kingdom . |
| WO 84/01327 | 4/1984 | WIPO . |
| 9014046 | 11/1990 | WIPO . |
| WO 90/14046 | 11/1990 | WIPO . |
| WO 91/04068 | 4/1991 | WIPO . |
| WO 91/17788 | 11/1991 | WIPO . |
| 9208512 | 5/1992 | WIPO . |
| WO 92/11893 | 7/1992 | WIPO . |

OTHER PUBLICATIONS

Article from Design Ovine Hoestche Celen USC, pp. 2–2, 3–1, to 3–4, 1991.

Article from Plastics & Rubber Weekly, "Chemistry Advance Offers New Materials", p. 8, "One Piece Catheter ", p. 8 Dec. 3, 1988.

Article from Plastics and Rubber International, "Medical Uses of Polymers", vol. 11, No. 3, Jun. 1986.

Articles from Plastics Technology, "Multi–Lumen Medical Tubing Line"and "Satellite Extruders for Coextrusion", pp. 39–41, Aug. 1987.

"Award Caps Bottle's Introduction", USA Today, Friday , Oct. 7 1983.

Broad, "Plastics Revolution: A Rush of New Uses", The New York Times, Nov. 1, 1983.

Carley, "A Plastics Primer", Modern Plastics Encyclopedia, pp. 4–8, 1988.

Chin et al., "Long–Term Results of Intraoperative Balloon Dilatation", The Jounal of Cardiovascular Surgery, 30:454–458, 1989.

Davey, "Pleated Balloon Catheter", Biomedical Materials, Apr. 1991.

Dobrin, "Balloon Embolectomy Catheters in Small Arteris, I Lateral Wall Pressures and Shear Forces", Surgery, vol. 90, no. 2, pp. 177–185, Aug. 1981.

Elastomerics, EuroNews by Maurice Botwell, "Dupont Uses New Design Concepts to Boost TP Elastomers in Europe", pp. 38–39, Nov. 1986.

Encyclopedia of Polymer Science and Engineering, vol. 2, "Biaxial Orientation", pp. 339–373.

"Extruded Tubing is Called on to Perform More Complex and Critical Surgical Jobs", Modern Plastics International, pp. 40–41, 1990.

"Film Laminate Key to Record Setting Balloon Flight", Plastics Design Forum, pp. 66–68, Mar./Apr. 1988.

Fogarty et al., "Intraoperative Coronary Artery Balloon Catheter Dilatation", American Heart Journal vol. 107, No. 4, pp. 845–851, Apr., 1984.

Fogarty et al., "Adjunctive Intraoperative Arterial Dilation", Arch. Surg., 116:1381–1397, 1981.

Fogarty, "The Balloon Catheter in Vascular Surgery", Review of Surgery, vol. 24, No. 1, pp. 9–19, 1967.

Forcinio, "Squeezable bottle ends long wait for ketchup", FOOD & DRUG PACKAGING, vol. 47, No. 10, Oct. 1983.

Giesy et al., "Coaxial and Linear Extrusion Balloon Catheters Compared to Guidewires...Urinary Tract", The Journal of Urology, vol. 133, No. 4, p. 238A, Apr. 1985.

Gisey et al., "Coaxial Balloon Dilation and Calibration of Urethral Strictures",The American Journal of Surgery, 147:611–614, May 1984.

Giesy et al., "Ureteral Access: Bypassing Impacted Stones...Balloon Catheter", The Journal of Urology, vol. 131, No. 4, 152A, 79th Annual Meeting of American Urological Association, Inc., May. 6–10, 1984.

Gruntzig et al., "Technique of Percutaneous Transluminal Angioplasty with the Gruntzig Balloon Catheter", American Journal of Roentgenology, vol. 132, No. 4, pp. 547–552, Apr. 1979.

Inoue, "A New Balloon Catheter for Percutaneous Transluminal Angioplasty", AJR 144:1069–1071, May. 1985.

Inoue et al., "Clinical Application of Transvenous Mitral Commissurotomy by a New Balloon Catheter", Journal of Thoracic and Cardiovascular Surgery, vol. 87, No. 3, pp. 394–402, Mar. 1984.

Jain et al., "In Vivo Assessment of Vascular Dilatation During Percutaneous Transluminal Coronary Angioplasty," American Journal of Cardiology, 60:968–982, Nov. 1987.

Irwin, Belcher, Bruning and Suit, Modern Plastics Encyclopedia, pp. 203–210, 1988.

Jain et al., "Effect of Inflation Pressures on Coronary Angioplasty Ballons", American Journal of Cardiology, 57:26–28, Jan. 1, 1986.

Jekell et al., "Balloon Catheters", Acta Radiological Diagnosis, 21:47–52, 1980.

Jensen, "Double–Lumen Balloon Catheter", Acta Radiological Diagnosis, 17:886–890, Nov. 1976.

Katzen et al., "Percutaneous Transluminal Angioplasty With the Gruntzig Balloon Catheter", Arch Surg., vol. 114, No. 12, pp. 1389–1399, Jun. 1979.

Kennedy et al., "Interventional Coronary Arteriography", Annual Review of Medicing: Selected Topics in the Clinical Sciences, 35:513–516, 1984.

Kent et al., "Percutaneous Transluminal Coronary Angioplasty: Report From...Blood Institute", The American Journal of Cardiology, vol. 49, pp. 2011–2020, Jun. 1982.

Kinney et al., "Shear Force in Angioplasty: It's Relation to Catheter Design and Function", American Journal of Roentgenology, 144:115–122, Jan. 1985.

LeMay et al., "Pinhole Balloon Rupture During Coronary Angioplasty Causing Rupture of the Coronary Artery", Catherization and Cardiovascular Diagnosis 19:91–92, 1990.

Letter from Modern Plastics, "Coextrusion Measurement by IR Sensors", Jun. 1984 14:8.

Levy, "Improved Dilation Catheter Balloons", Journal of Clinical Engineering, pp. 291–296, Jul./Aug. 1986.

Mobley et al., "Effects of Organophosphorus Agents on Sarcoplasmic Reticulum in Skinned Skeletal Muscle Fibres", Toxicology and Applied Pharmacology, 94:407–413, 1988.

"New Silicone–Modified TPE Combined Best of Both Worlds", Biomedical Elastomers, pp. 28–30, Nov. 1988.

Palmaz et al., "Expandable Intraluminal Graft: A Preliminary Study", Radiology, vol. 156 No. 1, Jul. 1985.

Palmaz et al., "Expandable Intrahepatic Portacaval Shunt Stents: Early Experience in the Dog", AJR 145:821–825, Oct. 1985.

"Polymer Structure, Properties and Applications", Rudolph D. Deanin, Ph.D., Professor of Plastics, Lowell Technological Institute, Table of Contents and pp. 196–220 Radiology, vol. 115, No. 3, Jun. 1975.

Reckner, "Testing by ASTM Methods", Modern Plastics Encyclodepia, pp. 318–320, 1988.

"Rigid Plastics Are Getting a Foot in the Kitchen Door", CHEMICAL WEEK, Oct. 12, 1983.

Shedd, Rader, Edenbaum et al., Willwerth et at., Gabbett, Peters, Tomanek et al., Clark, Modern Plastics Encyclopedia, pp. 93–109, 1988.

Sweeting et al., "Auxiliary Film Treatments"& "Polyethylene Terephthalate Film Structure and Analysis", The Science and Technology of Polymer Films, vol. II John Wiley & Sons, Inc., pp. 639, 1971.

Supplements to Circulation, An Official Journal of the American Heart Association, vols. 53 and 54, p. II–81, Jan.–Dec. 1976.

"Surface Analysis of Biomedical Materials and Devices – Part 1", Biomedical Polymers, vol. 4, No. 7, pp. 1–15, 1988.

"The Gamma Bottle", Food and Drug Packaging, vol. 47, No. 10, Oct. 1983.

Wholey, "A Newly Designed Angioplasty Catheter: 'The Gemini Balloon'", CardioVascular and Interventional Radiology, 11:42–44, 1988.

MULTILAYER CATHETER BALLOON

This is a division of application Ser. No. 08/692,314, filed on Aug. 5, 1996; now pending, which is a continuation of prior application Ser. No. 08/415,094, filed Mar. 31, 1995 abandoned; which is a continuation of application Ser. No. 08/105,353, filed Aug. 10, 1993 abandoned; which is a division of application Ser. No. 07/727,664, filed Jul. 9, 1991 U.S. Pat. No. 5,270,086; which is a continuation-in-part of Ser. No. 07/411,649, filed Sep. 25, 1989 abandoned.

BACKGROUND OF THE INVENTION

I. Field of the Invention

This invention relates generally to balloon catheters, and more particularly to a method for fabricating a multi-layer balloon composite exhibiting enhanced characteristics attributable to the properties of the individual layers.

II. Discussion of the Prior Art

As an alternative to open-heart, coronary bypass surgery, a technique referred to coronary transluminal angioplasty has been developed following the pioneering introduction of the technique by A. Gruntzig. In carrying out this procedure, a dilatation catheter having an inflatable expander member (balloon) on the distal end thereof is routed through the vascular system to a location within a coronary artery containing a stenotic lesion. Following placement of the expander member across the lesion, a fluid is introduced into the proximal end of the catheter and is used to inflate the expander member to a predetermined relatively high pressure whereby the lesion is compressed into the vessel wall restoring patency to the previously occluded vessel.

It is desirable that the composite expander member exhibit the following characteristics:
1. High burst (tensile) strength;
2. Low radial expansion at elevated pressures;
3. Ease of bonding to a catheter body;
4. Failure characteristics avoiding pinhole ruptures; and
5. Low coefficient of friction.

The Schjeldahl et al. U.S. Pat. No. 4,413,989 owned by applicants' assignee discloses a coronary transluminal angioplasty catheter in which the expander member is formed from polyethylene terephthalate in a drawing and blow molding process so as to provide biaxial orientation to the material. Such PET balloons are found to exhibit the desirable property of high burst strength and relatively low radial expansion when inflated to seven atmospheres or more. However, because the catheter body itself is generally fabricated from a formulation containing silicon rubber, polyethylene, PET or polyurethane, a problem exists when attempts are made to bond the expander member to the distal end portion of the catheter body. The PET polyester balloon tends not to adhere easily to the catheter body especially in a thermal bonding process.

Moreover, experience with polyethylene, PVC and polypropylene expansion members has shown that at relatively high pressures, pinhole leaks form which may create a high velocity jet of inflation fluid capable of perforating the blood vessel when it impinges on the vessel wall. Thus, it would be desirable if the expander member can be fabricated in such a way that it exhibits a controlled mode of failure, i.e., a rapid rupture so that the pressure is released over a significant area in a short time frame.

SUMMARY OF THE INVENTION

The above-listed desirable characteristics are achieved in accordance with the present invention by forming a multi-layer balloon where the individual layers afford a desirable property to the composite. It has been found that a layer of medium or relatively high melt temperature material which also exhibits high tensile strength with relatively low distensibility can be used to provide the required high burst or tensile strength and low radial expansion at high pressures required by the expander member in a composite structure. This layer may be referred to as the tensile layer or tensile ply. It may be a biaxially-oriented film of relatively high crystallinity.

In the composite structure, the tensile layer is combined as an outer layer with a chemically and physically compatible adhesion or bonding inner layer which is fabricated from materials having superior glue bonding or melt bonding characteristics. The bonding layer also must have good interlayer adhesion characteristics with the material used for the tensile layer. The bonding layer imparts the necessary adhesion properties to properly bond the expander member to the distal end portion of the catheter body. If melt bonding is the desired mode, the material of the bonding layer should have a lower melting point than that of the tensile layer so that melt bonding of the composite may be readily achieved in the fabrication process with minimal effect on the tensile ply. In this regard, it should be noted that the bonding layer may or may not be continuous or coextensive with the entire inner surface of the tensile layer inasmuch as it is required generally only in the vicinity of the expander/catheter interface surfaces.

Examples of materials exhibiting the required high tensile, low distensibility and having medium melt temperatures include certain copolymers such as ABS (acrylonitrile-butadiene-styrene), ABS/nylon, ABS/polyvinyl chloride (PVC) and ABS/polycarbonate. Such materials having high melt temperatures include acrylonitrile copolymer, polyacrylamide, polyacrylate and polyacrylsulfone. Other materials having suitable characteristics include high melt temperature polyesters such as polyethylene terephthalate (PET), polybutylene terephthalate (PBT), polyethylene naphthalate (PEN), liquid crystal polymer (LCP), polyester/polycaprolactone and polyester/polyadipate; and high melt temperature polyethers including polyetheretherketone (PEEK), polyethersulfone (PES), polyetherimide (PEI) and polyetherketone (PEK), polymenthylpentene, polyphenylene ether, polyphenylene sulfide, and styrene acrylonitrile (SAN). It should be noted that LCP has a very high melt temperature and SAN, a lower melt temperature than the other listed polyethers. Additional compounds having the required tensile properties which have a medium melt temperature include polyamides such as nylon 6, nylon 6/6, nylon 6/66, nylon 6/9, nylon 6/10, nylon 6/12, nylon 11 and nylon 12.

Suitable adhesion materials for the bonding layer having a high distensibility but excellent melt bond and glue adhesion properties with relatively low melt temperatures include ethylene, propylene, ethylene vinylacetate and ethylene vinyl alcohol (EVA), various ionomers, polyethylene type I-IV, polyolefins, polyurethane, polyvinyl chloride, and polysiloxanes (silicones). Those with low to medium melt temperatures include fluorocarbons such as polychlorotrifluoroethylene (CTFE), poly[ethylene-co-chlorotrifluoroethylene] (ECTFE), copolymer ethylene tetrafluoroethylene (ETFE), copolymer tetrafluoroethylene and hexafluoropropylene (FEP), perfluoroalkane (PFA) and poly[vinylidene fluoride] (PVDF).

It will be appreciated that the particular combination chosen would depend on the particular application and particular catheter involved, and that an array of multilayer expanders of different composition combinations particularly applicable to different situations can be produced. In addition, specific properties required for addressing a specific stenosis could be utilized to produce a tailor-made expander.

More particularly with respect to the process, a tubular parison is first generated in a co-extension process whereby different polymeric materials are coaxially layered. Subsequently, the parison is inserted in a blow molding fixture, allowing the tube to be longitudinally drawn and radially expanded until the composite film is oriented, the maximum O.D. of the expander member is defined and a desired film thickness is achieved. For example, in forming the parison, PET of a predetermined viscosity may be coextruded with polyethylene where, forming the parison, the polyethylene lines the lumen thereof. When the expander member is formed from the parison in the blow molding operation, the PET layer affords the desired burst strength and limited radial expansion characteristic while the polyethylene layer enhances the ability to bond the resulting balloon to the catheter body.

The characteristic of lubricity may also be added by coating the exterior of the composite with a suitably lubricious plastic exhibiting high hydrophilic characteristics. Suitable lubricious hydrophilic materials include polycaprolactam polyvinylindol, N-vinylpyrrolidone, various hydrogels, and other hydrophilic lubricious polymeric materials.

One successful embodiment of the system of the invention utilizes a combination of polyethylene terephthalate (PET) as the tensile layer in combination with a bonding layer of polyethylene. The composite PET/polyethylene balloon was coated on the exterior of the PET with polycaprolactam. By forming a three-layer tubular parison having a layer of plastic with known rupture characteristics, the polyethylene layer may provide the bondability attribute, the PET, the limited radial expansion characteristic and/or the controlled rupture characteristic while polycaprolactam again affords the lubricity.

Of course, the known rupture or failure characteristics involve the failure by bursting or large scale rupture of the tensile layer rather than the development of small or pin hole leaks in which a small stream of high pressure fluid is released. This minimizes possible damage to surrounding tissue caused by high pressure fluid leakage from the membrane.

DESCRIPTION OF THE DRAWINGS

The various features, characteristics and advantages of the invention will become apparent to those skilled in the art from the following detailed description of a preferred embodiment, especially when considered in conjunction with the accompanying drawings in which.

DESCRIPTION OF THE PREFERRED EMBODIMENT

Figure 1:
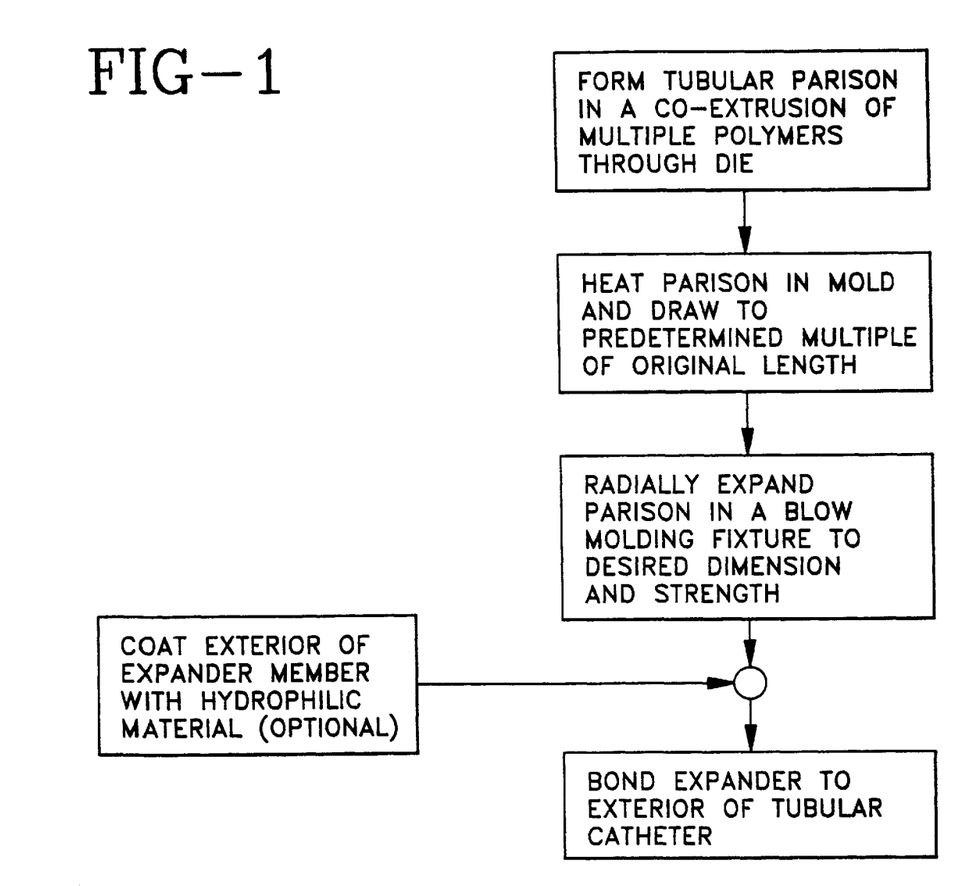
FIG. 1 is a process flow chart illustrative of the present invention.
Figure 2:
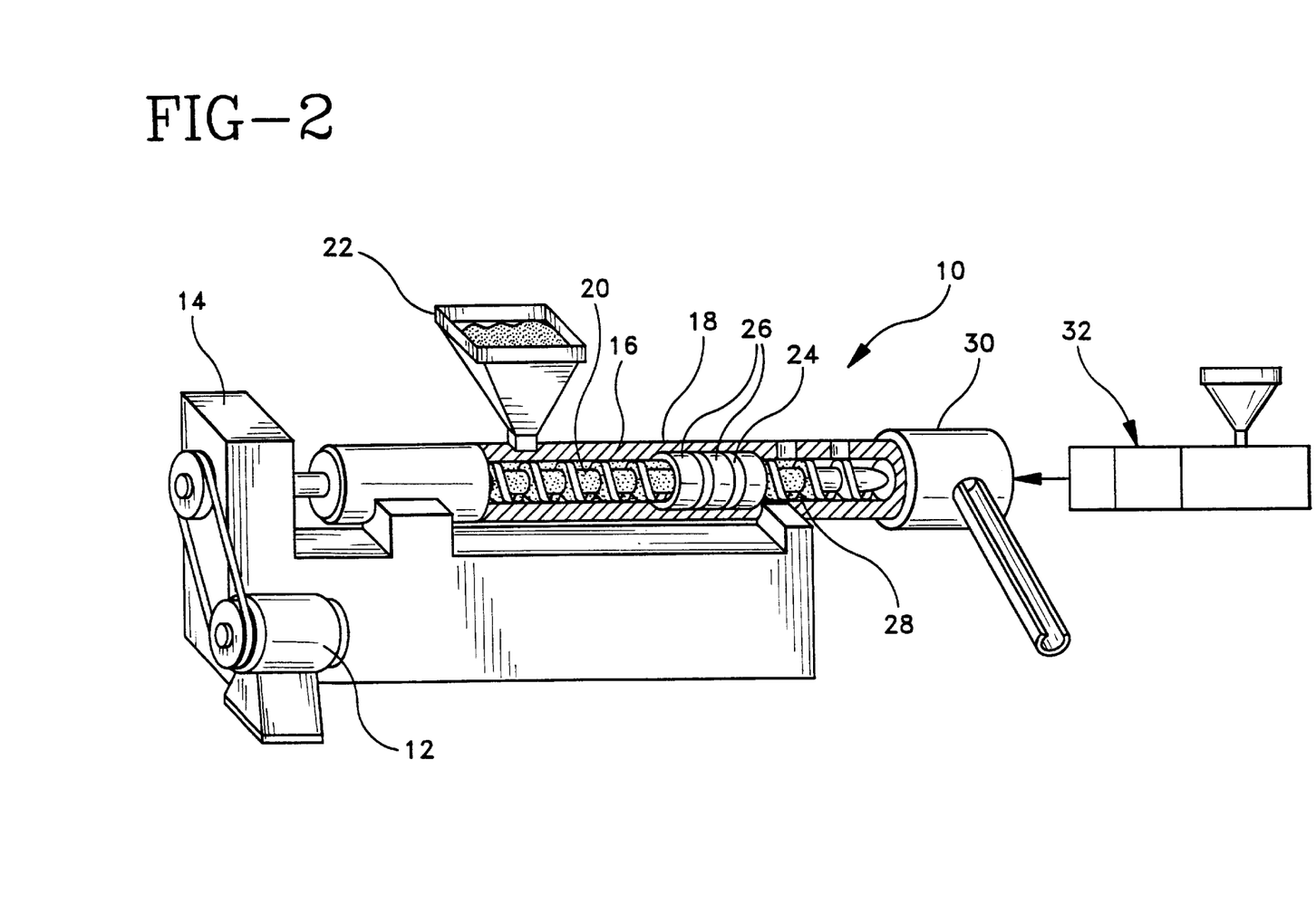
FIG. 2 is a partial schematic illustration of apparatus for manufacturing parisons in a co-extrusion process.

With reference to FIG. 1, in fabricating the multilayer expander member in accordance with the present invention, the first step in the process is to create a parison which, when heated and then drawn and blown creates a balloon or expander member for use on an intravascular catheter. The extruding apparatus is indicated generally by numeral 10 in FIG. 2 and is seen to comprise a motor 12 coupled in driving relationship to a gear box 14 whose output shaft comprises a coarse-pitched archimedian screw 16 rotating within a heated barrel 18. In accordance with known practice, the screw generally has three distinct sections. In the "feed" section 20, directly beneath the feed hopper 22, the screw channel depth is constant and relatively large and serves to convey solid polymer material from the hopper. The depth of the flute in the "compression" section 24 is uniformly tapered and designed to compact the plastic and force it into contact with the barrel 18 to enhance melting. The melting is achieved mainly by a combination of heat conducted from electrical heating elements 26 contained in the barrel and the heat generated by the intense shearing in the molten layer formed between the barrel and the solid material. Numeral 28 identifies the "metering" section of the screw in which the flute depth is constant and relatively small. It controls the output from the extruder in terms of quantity, steadiness and homogeneity. Disposed at the end of the screw 16 is an extruder die 30 which, in the case of the present invention, provides for co-extrusion of at least two different plastics. The first plastic passing through extruder 10 combines with a second plastic exiting a substantially identical extruder shown schematically at 32 to create a concentrically layered tubular parison, the cross-section of which is seen in the view of FIG. 4.

Figure 3:
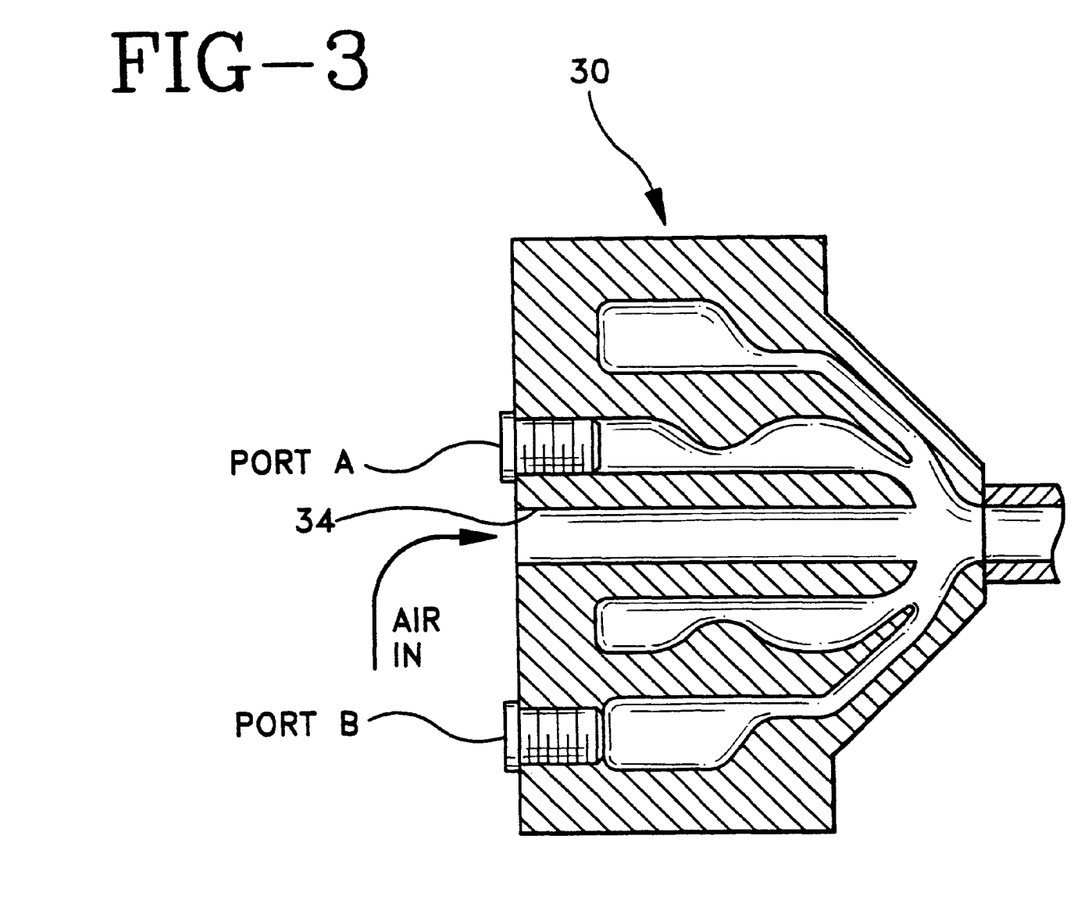
FIG. 3 is a cross-sectional view of a two-component co-extrusion die useful in forming a two-layer parison.

FIG. 3 is a cross-sectional view taken through a two-port co-extrusion die. For example, the output from the metering section 28 of the extruder 10 may be fed into die port A in FIG. 3 while that from the metering section of the screw of extruder 32 feeds port B. The molten plastic flows together to form a layer with the plastic entering port B surrounding the plastic entering port A. As the plastic is made to flow through the die, air is also introduced through the central bore 34 of the die 30 to prevent the collapse of the tubular shaped exudate.

In accordance with one aspect of the invention, the plastic entering port A, for example, may comprise a polyolefin or PVC while that forced into port B may be a homopolyester, preferably PET, of a predetermined viscosity. With these two constituents, the resulting tubular parison will have the PVC as the inner tubular layer and the PET as its outer layer. The thickness of the individual layers will be determined by the mass flow ratios provided by the respective extruders. The final diameter of the parison is determined by the size of the die exit opening, the total flow of material into ports A and B and the take-away or draw speed.

Figure 4:
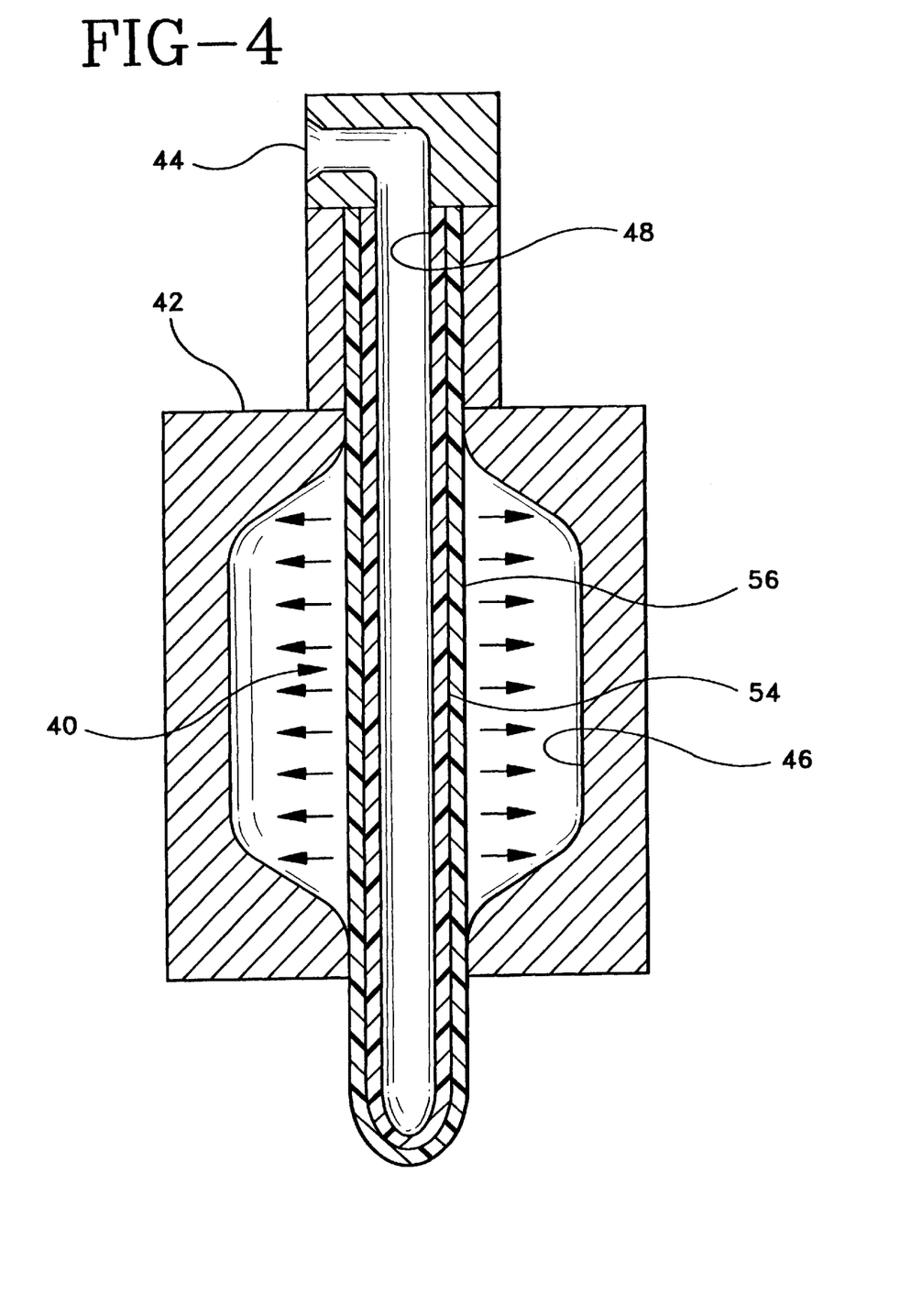
FIG. 4 illustrates schematically an apparatus for blow molding the parison into a biaxially oriented multilayer expander member.

The balloon itself is fabricated in a blow molding operation wherein the parison 40 is inserted into the blow mold 42 as shown in FIG. 4 and air or other suitable fluid is introduced through the port 44 at a predetermined pressure. The mold 42 has a cavity 46 corresponding to the desired size of the balloon to be produced.

After the tubular parison is disposed in the mold, the mold is heated to thereby raise the tubing temperature to a point between the second order transition temperature and the first order transition temperature of the polyester polymer.

Of course, the inner layer can be caused to adhere to and attach the balloon to the exterior of the tubular catheter body in any desired manner. The material of the inner layer may be such that relatively low melt temperature material can be utilized to achieve a permanent melt bond. Preferably, the exterior of the tubular catheter body is provided with a coating of the same or similar material to that of the inner layer of the multilayer balloon structure such that the materials bonded are substantially identical. This also allows the continuous joint to be made utilizing melt bonding the materials. In this regard, it is desired that the material forming the bonding layer of the multilayer system have a melting temperature sufficiently below that of the material of the tensile layer so that the melt bonding can be achieved without affecting the future physical characteristics of the system.

As described above, it is desirable that the expander member itself exhibits rather high tensile strength properties. This means exhibiting a burst pressure well in excess of 7 atmospheres while undergoing a radial expansion less than about 3–10 percent. The actual strength, of course, will depend on the relative tensile strength of the material and thickness of the material layer. In addition, these extruded materials are ones not prone to pinhole leaks in the process of the invention in most cases results in a mode of failure, should failure occur, in the form of a rapid rupture which releases the internal pressure over a considerable area in a short time frame so that damage to the vessel is minimized.

Figure 5:
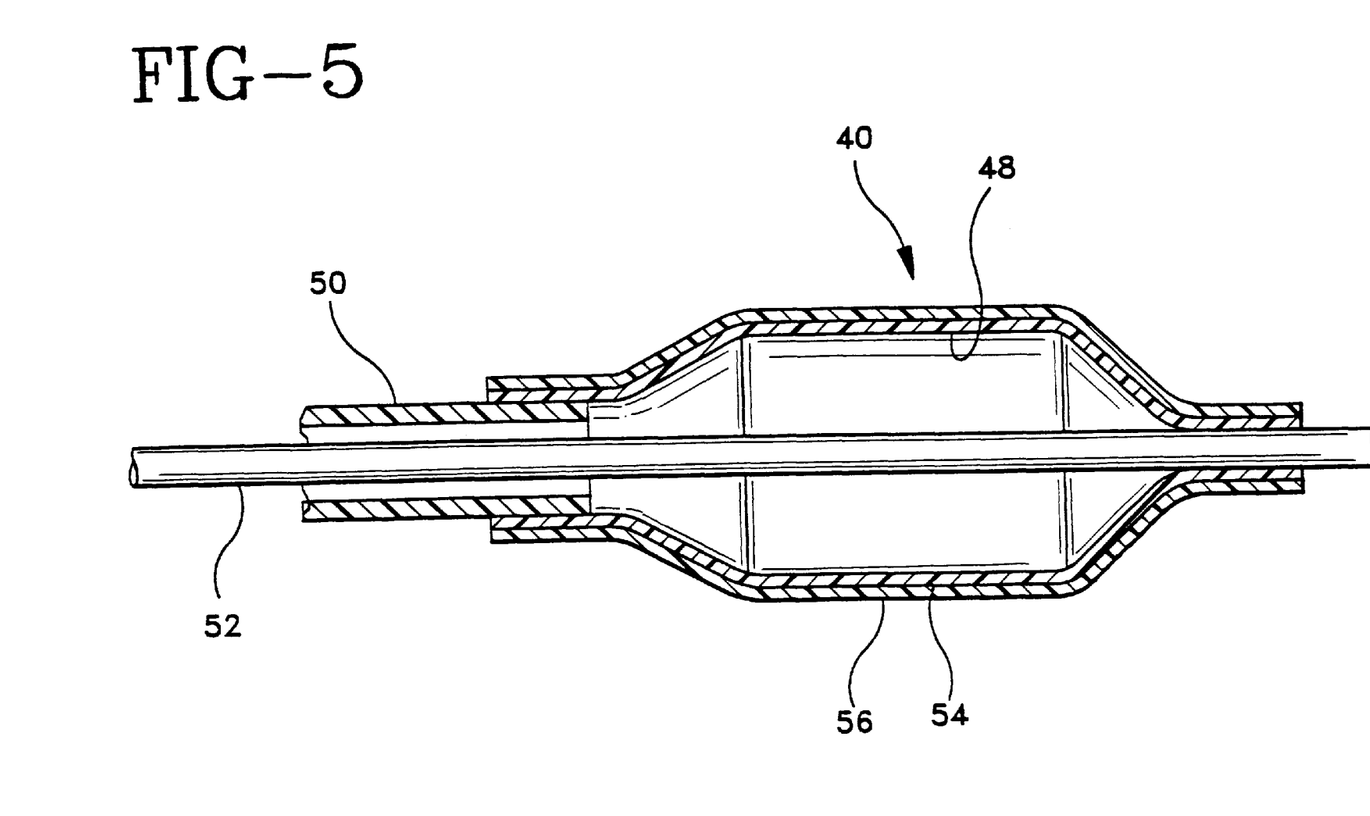
FIG. 5 shows the expander joined to the distal end of a catheter.

By first drawing the tubular parison and subsequently blow molding same, biaxial orientation takes place whereby the PET layer 56, while remaining flexible, becomes strong as regards the inflation pressure at which the material will burst. When it is desired to bond the finished balloon onto the catheter body as illustrated in FIG. 5, the inner layer 48 of PVC can readily be bonded to an outer PVC tubular body 50 and to an inner tubular body 52, such as by adding adhesive 54 between the outer layer 56 and the inner layer 48. The space between the coaxially disposed tubes allows for injection of a balloon inflation fluid. Balloons produced in accordance with the invention may exhibit a burst pressure well in excess of 7 atmospheres while radially expanding less than about 3–10 percent. While the PVC layer 48 adds little to the burst strength of the composite, it does facilitate the attachment of the balloon to the exterior of the tubular catheter body.

If it is desired to increase the lubricity of the composite balloon, this may be accomplished by dipping or other coating the multilayer balloon in a suitable hydrophilic material such as polyvinylidol, N-vinylpyrolodone, hydrogels, etc.

Figure 6:
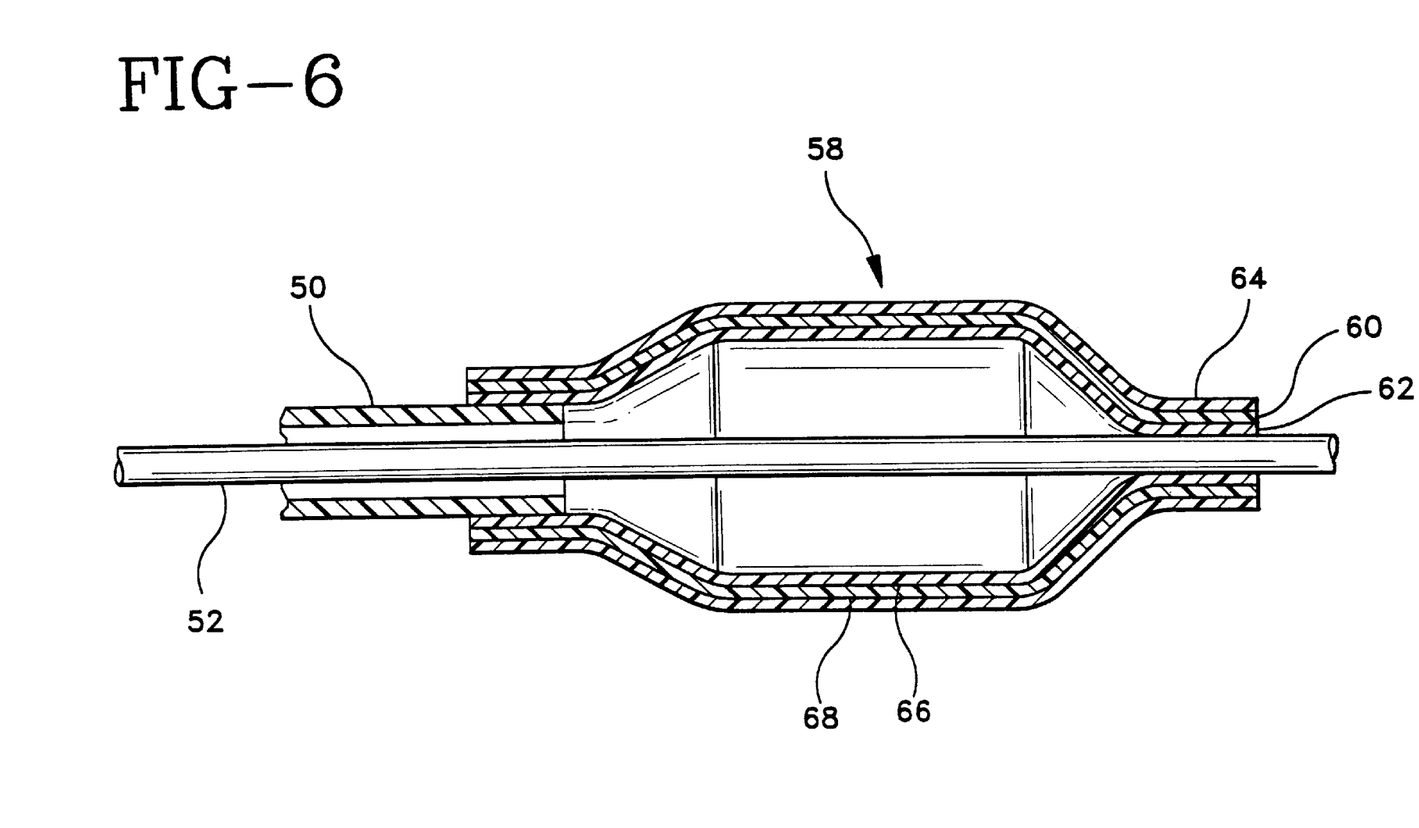
FIG. 6 depicts an alternative embodiment of the multilayer expander member.

With reference to FIG. 6 and rather than utilizing PET in combination with PVC, a balloon having enhanced properties maybe created by co-extruding a high molecular weight crystalline polyester 60 with a lower molecular weight amorphous polyester 62 in forming the parison. An outer layer of filled polymer 64 adds lubricity. As known in the art, adhesive 66, 68 may be juxtaposed between layers 60, 62 and 64. Following drawing and radial expansion in a blow molding operation, the resulting balloon is found to exhibit high burst strength, low radial expansion and superior bondability as compared to conventional PET single-layer balloons.

The rupture characteristics of a polymer layer can be modified to increase the rupture rate by adding filler material. The filler materials may be an inert type, such as calcium carbonate, generally in powder form, carbon in fiber form, or an incompatible second phase polymer. Incompatible phase polymer systems afford many advantageous characteristics and are a function of the dispersion between the two phases. Materials which might be candidates for this are polypropylene and selected rubbers, polyester and polypropylene.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. An expandable catheter balloon comprising:
   (a) a first layer comprising a first biaxially oriented polymer; and
   (b) a second layer adhered to the first layer and comprising a second biaxially oriented polymer other than the first biaxially oriented polymer;
   the balloon being sized and configured for coronary transluminal application and having a burst pressure in excess of 7 atmospheres.

2. The balloon of claim 1 wherein the second layer consists essentially of biaxially oriented polyolefin.

3. The balloon of claim 2 wherein the second layer consists essentially of biaxially oriented polyethylene.

4. The balloon of claim 1 wherein the first layer is an outermost layer of the balloon.

5. The balloon of claim 1 wherein the second layer is an innermost layer of the balloon.

6. The balloon of claim 1 further comprising a lubricious coating on an outermost layer of the balloon.

7. The balloon of claim 1 wherein the first biaxially oriented polymer is more crystalline than the second biaxially oriented polymer.

8. The balloon of claim 7 wherein the second layer consists essentially of biaxially oriented polyester.

9. The balloon of claim 1 further comprising a third polymeric layer adhered to one of the first or second layers.

10. An expandable catheter balloon comprising:
    (a) a first layer comprising biaxially oriented polyester; and
    (b) a second layer adhered to the first layer and comprising biaxially oriented polymer other than the biaxially oriented polyester of the first layer;
    the balloon being sized and configured for coronary transluminal application and having a burst pressure in excess of 7 atmospheres.

11. The balloon of claim 10 wherein the first layer consists essentially of biaxially oriented polyethylene terephthalate co-polyester or homopolyester.

12. The balloon of claim 11 wherein the first layer consists essentially of biaxially oriented polyethylene terephthalate homopolyester.

13. The balloon of claim 11 wherein the first layer consists essentially of biaxially oriented polyethylene terephthalate co-polyester.

14. The balloon of claim 10 wherein the second layer consists essentially of biaxially oriented polyolefin.

15. The balloon of claim 14 wherein the second layer consists essentially of biaxially oriented polyethylene.

16. The balloon of claim 10 wherein the first layer is an outermost layer of the balloon.

17. The balloon of claim 10 wherein the second layer is an innermost layer of the balloon.

18. The balloon of claim 10 further comprising a lubricious coating on an outermost layer of the balloon.

19. The balloon of claim 10 wherein the biaxially oriented polyester of the first layer is more crystalline than the biaxially oriented polymer of the second layer.

20. The balloon of claim 19 wherein the second layer consists essentially of biaxially oriented polyester other than the biaxially oriented polyester of the first layer.

21. The balloon of claim 10 further comprising a third polymeric layer adhered to one of the first or second layers.

22. An expandable angioplasty catheter balloon comprising:

(a) a first layer consisting essentially of biaxially oriented polyester; and (b) a second layer adhered to the first layer and consisting essentially of biaxially oriented polyolefin;

the balloon being sized and configured for coronary transluminal angioplasty and having a burst pressure in excess of 7 atmospheres.

23. The balloon of claim 22 wherein the second layer consists essentially of biaxially oriented polyethylene.

24. The balloon of claim 22 wherein the first layer consists essentially of biaxially oriented polyethylene terephthalate.

25. The balloon of claim 24 wherein the second layer consists essentially of biaxially oriented polyethylene.

* * * * *